(12) United States Patent
Rimlinger et al.

(10) Patent No.: US 8,337,467 B2
(45) Date of Patent: Dec. 25, 2012

(54) SAFETY DEVICE FOR A SYRINGE (75) Inventors: Thierry Rimlinger, L'Isle d'Abeau
(FR); Michel Pouget, Domarin (FR);
Philippe Dodier, St Foy les Lyon (FR)

(73) Assignee: Rexam Healthcare La Verpilliere, La
Verpilliere (FR)

( * ) Notice: Subject to any disclaimer, the term of this
patent is extended or adjusted under 35
U.S.C. 154(b) by 1408 days.

(21) Appl. No.: 10/492,625

(22) PCT Filed: Oct. 15, 2002

(86) PCT No.: PCT/FR02/03529
§ 371 (c)(1),
(2), (4) Date: Jan. 3, 2005

(87) PCT Pub. No.: WO03/033059
PCT Pub. Date: Apr. 24, 2003

(65) Prior Publication Data
US 2006/0036216 A1    Feb. 16, 2006

(30) Foreign Application Priority Data
Oct. 15, 2001 (FR) ...................................... 01 13256

(51) Int. Cl.
*A61M 5/32*    (2006.01)
*A61M 25/00*   (2006.01)
(52) U.S. Cl. ........................................ 604/198; 604/263
(58) Field of Classification Search .................. 604/110,
604/192–198, 263
See application file for complete search history.

(56) References Cited

U.S. PATENT DOCUMENTS

| 3,667,465 | A | * | 6/1972 | Voss ................................ 604/59 |
| 4,220,151 | A | * | 9/1980 | Whitney ....................... 604/110 |
| 4,850,977 | A | * | 7/1989 | Bayless ......................... 604/198 |
| 4,863,434 | A | * | 9/1989 | Bayless ......................... 604/198 |
| 4,927,416 | A | * | 5/1990 | Tomkiel ........................ 604/198 |
| 5,163,918 | A | * | 11/1992 | Righi et al. .................... 604/198 |
| 5,167,640 | A | * | 12/1992 | Balding ......................... 604/192 |
| 5,176,656 | A | * | 1/1993 | Bayless ......................... 604/198 |
| 5,197,953 | A | * | 3/1993 | Colonna ........................ 604/110 |
| 5,342,320 | A | * | 8/1994 | Cameron ....................... 604/192 |
| 5,437,647 | A | * | 8/1995 | Firth et al. ..................... 604/110 |
| 5,478,316 | A | * | 12/1995 | Bitdinger et al. ............. 604/135 |
| 5,492,536 | A | * | 2/1996 | Mascia .......................... 604/197 |
| 5,562,624 | A | * | 10/1996 | Righi et al. .................... 604/110 |
| 5,562,626 | A | * | 10/1996 | Sanpietro ...................... 604/110 |
| 5,681,291 | A | * | 10/1997 | Galli ............................... 604/192 |
| 5,855,839 | A | * | 1/1999 | Brunel ........................... 264/524 |

(Continued)

FOREIGN PATENT DOCUMENTS
FR         2 788 986         8/2000
(Continued)

*Primary Examiner* — Kevin C Sirmons
*Assistant Examiner* — Andrew Gilbert
(74) *Attorney, Agent, or Firm* — Oliff & Berridge, PLC (57) ABSTRACT

The invention relates to a safety device (1) for a syringe (2), the device comprising a protective sheath (20) in which the syringe (2) can slide, said sheath (20) presenting an opening (36) at a distal portion (33), which opening is suitable for allowing the syringe (2) to project beyond the sheath (20). According to the invention, the sheath (20) presents radial resilience at its distal portion (33) suitable for enabling the sheath (20) to receive a cylinder (3, 19) of diameter greater than that of said opening (36).

22 Claims, 8 Drawing Sheets

U.S. PATENT DOCUMENTS

| | | | |
|---|---|---|---|
| 6,033,387 A * | 3/2000 | Brunel | 604/198 |
| 6,224,575 B1 * | 5/2001 | Garvin | 604/195 |
| 6,361,525 B2 * | 3/2002 | Capes et al. | 604/240 |
| 6,419,658 B1 * | 7/2002 | Restelli et al. | 604/110 |
| 6,458,101 B1 * | 10/2002 | Hu | 604/110 |
| 7,875,006 B2 * | 1/2011 | Pessin | 604/192 |
| 2005/0165353 A1 * | 7/2005 | Pessin | 604/110 |
| 2006/0184133 A1 * | 8/2006 | Pessin | 604/198 |
| 2006/0189931 A1 * | 8/2006 | Riemelmoser | 604/110 |

FOREIGN PATENT DOCUMENTS

| | | |
|---|---|---|
| WO | WO 93/00949 | 1/1993 |
| WO | WO 00/33900 | 6/2000 |
| WO | WO 01/41841 A2 | 6/2001 |
| WO | WO 01/60435 A1 | 8/2001 |

* cited by examiner

FIG_1    FIG_2

FIG_8

FIG_9

FIG.10

FIG_11

FIG_12

FIG_13

FIG_14

FIG_15   FIG_16

FIG_17

FIG_18

FIG_19

SAFETY DEVICE FOR A SYRINGE

The present invention relates to a safety device for a syringe, in particular a prefilled syringe, enabling the needle thereof to be protected after injection.

European patent application EP 0 966 983 discloses a safety system for a prefilled syringe, comprising a needle protection jacket engaged around the syringe and situated inside a sheath, said jacket being suitable for sliding relative to the needle and to the sheath. At the end of injection, a spring causes the protective jacket to be expelled out from the sheath so that said jacket comes to cover the needle.

That system presents a certain number of drawbacks.

In order to expel the jacket, the user must exert relatively strong pressure on the head of the syringe piston in order to cause an abutment on the jacket to go past an abutment on the sheath. In other words, the user must perform an additional action following the action that gives rise to injection.

In addition, in the event of the user causing the jacket to be expelled while the syringe is still close to the patient, the jacket will strike the skin of the patient and might injure the patient.

If the user moves the syringe further away prior to causing the jacket to be expelled, then the needle remains unprotected while the syringe is being taken further away, and that presents a risk of accidental contamination and/or injury.

French patent application FR 2 799 375 discloses an injector device comprising a syringe and a device for protecting the needle after use. That protection device comprises a locking ring having the syringe fixed therein, with the resulting assembly being slidably engaged in a protective case. At the end of injection, a spring causes the above-mentioned assembly to move in such a manner that the needle is withdrawn into the protective case.

That device presents relatively large size in the axial direction.

International patent application WO 00/33900 in the name of the Applicant company discloses a safety assembly for a prefilled syringe comprising a tubular sheath into which the syringe cylinder is inserted directly and is movable axially between an active, injection position and a position for protecting the needle.

The present invention seeks to propose a safety device for a needle that can be actuated at the end of injection in a manner that is simple and that does not require any additional action on the part of the user.

The present invention also seeks to provide a safety device which is adapted to at least two types of syringe, enabling syringes to be used in a manner that is both convenient and safe, and that is also convenient and inexpensive to make.

In a first aspect, the present invention thus provides a safety device for a syringe, in particular a prefilled syringe, the syringe comprising a cylinder with a head at its proximal end, a needle carrier situated at the distal end of the cylinder and provided with a needle, a piston mounted to move in the cylinder, and a piston rod suitable for pushing the piston, the device being characterized by the fact that it comprises a sleeve suitable for receiving the syringe cylinder, the sleeve having grip means at its proximal portion for gripping the syringe head and suitable for gripping syringes of at least two different types, and by the fact that the device further comprises both a protective sheath in which the assembly constituted by the syringe and the sleeve can slide between a first position enabling injection to be performed and a second position in which the syringe needle is withdrawn inside the protective sheath, and a resilient element acting between said sheath and said assembly, enabling said assembly to be moved at the end of injection from the first position into the second position by said assembly moving in reverse relative to the sheath.

The safety device of the invention is intended for single use and is adapted to standard syringes of the kind available on the market, which are manufactured in large quantities and at relatively low cost.

In addition, because of its means for gripping the syringe head, the safety device is adapted to a plurality of syringe types, thus enabling a user to have a single type of safety device for fitting to a plurality of types of syringe, in particular 0.5 milliliter (mL) syringes and 1 mL syringes.

The resilient element causes the syringe and the sleeve to move rearwards inside the protective sheath, and this is particularly advantageous insofar as the protective sheath does not run any risk of striking the skin of the patient and of injuring the patient, unlike the system described in above-cited European patent 0 966 983 in which the protective jacket is expelled forwards.

The above-mentioned grip means are advantageously made at the proximal end of the sleeve, thus enabling the axial extent of the device to be kept small.

The grip means may comprise at least two elastically-deformable grip tabs connected to a collar of the sleeve, the syringe head being gripped against said collar by the two tabs.

In a variant, the grip means comprise a collar connected by a plurality of bridges of material to a top ring, the syringe head being retained between the collar and the top ring.

The top ring may define an opening of axial section that is generally frustoconical, diverging upwards, thus making it easier to engage the syringe head in said ring.

The protective sheath may include, in particular at its proximal end, elastically-deformable retaining tabs suitable for retaining the assembly constituted by the syringe and the sleeve in the first position and suitable for being deformed so as to release said assembly, enabling it to slide axially relative to the sheath and to pass into the second position.

The retaining tabs may be moved apart in relatively simple manner without requiring the user to exert a large force, the user not being required to perform any additional action to actuate the safety device other than the conventional action of making an injection.

The retaining tabs may serve as abutments for the sleeve so that the syringe secured to the sleeve is prevented from moving in translation relative to the protective sheath when the user causes the needle to penetrate under the patient's skin.

The piston rod of the syringe may include a pushbutton arranged in such a manner as to act directly on the retaining tabs.

This makes it possible to reduce the number of component parts in the safety device, which can be of relatively low cost price.

In a variant, the device includes an unlocking element that is distinct from the syringe, and that is movable relative to the sheath and suitable for acting on the retaining tabs.

Each of the above-mentioned grip tabs may include a surface against which a retaining tab comes to bear.

In a variant, the retaining tabs come to bear on the collar of the sleeve.

The retaining tabs are preferably arranged in such a manner as to be moved apart when they are actuated.

The above-mentioned unlocking element may include a button that is distinct from the sleeve and that is fitted on the sheath.

In a variant, the button is made integrally with the sleeve, in which case the button may include a wall connecting it to the remainder of the sheath via a plurality of resilient arms.

Advantageously, the sheath includes a collar serving as a bearing surface for the fingers of a user.

The sheath may include an inside wall that can be continuous, or that is preferably discontinuous and against which the resilient element comes to bear.

In its distal portion, the sleeve may include studs suitable for coming into contact into abutment against the above-mentioned bearing surface when the device moves into its protective, second position at the end of injection.

In an embodiment of the invention, the sleeve comprises a solid-walled cylindrical tube.

This tube may be rigid and may include, preferably at its distal end, a plurality of the above-mentioned studs, preferably two studs.

The protective sheath may include a plurality, and preferably four, longitudinally-extending guide splines. These splines are disposed in pairs, and the splines in each pair are spaced apart by a predetermined distance enabling a stud of the sleeve to engage between them.

In an embodiment of the invention, the splines are continuous, and one of the splines in each pair comes to an end before the other spline so as to define a bottom passage enabling a stud of the sleeve to be inserted between the two splines by turning the sleeve relative to the sheath. For example, one of the splines may be shorter than the other.

In another embodiment of the invention, one of the splines in each pair is discontinuous and includes a passage enabling a stud of the sleeve to be engaged therein and to be positioned between the two splines of the pair, and the sheath may include at least one portion in relief made on its inside wall and against which a stud comes into abutment while the sleeve is being inserted into the sheath, thus serving to position the stud in register with the above-mentioned passage.

The stud is inserted into the passage by turning the sleeve relative to the sheath through a predetermined angle, e.g. through about one-fourth of a turn when the sheath has two pairs of splines.

After being turned in this way, the sleeve guided by the guide splines is subjected to axial displacement inside the sheath until the retaining tabs are engaged on the grip means of the sleeve.

In another embodiment of the invention, the distal portion of the sleeve includes longitudinal slots defining elastically-deformable tabs having the above-mentioned studs made thereon.

The device advantageously includes anti-return means that act when the sleeve and the syringe are in the second position to oppose said assembly sliding out from the sheath, said means possibly comprising elastically-deformable locking tabs made on the protective sheath, said above-mentioned studs of the sleeve being suitable for going past said locking tabs when the sleeve goes from the first position to the second position, and the locking tabs serving as abutments for the studs once the studs have gone past them.

The sheath and the sleeve may be made as respective single-piece parts.

The resilient element, e.g. a helical spring, may bear against a surface of the sleeve.

The protective sheath may be made of a material that is transparent or semitransparent.

In a second aspect, the invention provides a safety device for a syringe, the device comprising a protective sheath in which the syringe can slide, said sheath presenting an opening at a distal portion, which opening is suitable for allowing the syringe to project beyond the sheath, the device being characterized in that the sheath presents radial resilience at its distal portion suitable for enabling the sheath to receive a cylinder of diameter greater than that of said opening.

By way of example, the cylinder is a cap for protecting the needle of the syringe. Under such conditions, the sheath serves to grip the cap firmly before the syringe is used, thus preventing any accident and protecting the needle from contamination prior to injection.

The cylinder may also be the cylinder of the syringe, in particular when the syringe is about to be used. This ensures that the syringe is gripped firmly in the sheath, thus improving safety and accuracy of injection.

For a sheath that can be made by molding, the above-mentioned cylinder may also be constituted by a moving portion of the mold used for making the sheath. The radial resilience of the sheath makes it easy to withdraw the moving portion from the mold during unmolding.

In an embodiment, the distal portion of the sheath is frustoconical in shape.

In addition, the distal portion of the sheath may be split so as to improve the radial resilience of the sheath. Thus, in an embodiment, the distal portion of the sheath has a plurality of longitudinal slots defining converging resilient tongues.

The safety device may further include means for enabling the syringe to slide in the sheath between a first position enabling injection to be performed and a second position in which the needle of the syringe is withdrawn into the inside of the sheath.

In an embodiment, the safety device includes a sleeve suitable for receiving the cylinder of the syringe, the sleeve having grip means at its proximal end for gripping the head of the syringe and suitable for gripping syringes of at least two different types, the assembly constituted by the syringe and the sleeve being capable of sliding between the first and second positions.

Preferably, the grip means are arranged to grip a collar forming the head of the syringe.

There may also be provided a resilient element acting between the sheath and the assembly constituted by the sleeve and the syringe, and enabling said assembly to be caused to move, at the end of injection, from the first position into the second position by a rearward movement of said assembly relative to the sheath.

The invention also provides an assembly comprising a syringe and a safety device as described above and fitted with said syringe.

The assembly may also include a cap protecting the needle of the syringe. By way of example, said cap is mounted in such a manner as to project beyond the sheath through the distal opening thereof.

Preferably, the sheath and the cap are arranged in such a manner as to act, after the cap has been removed, to prevent the cap from being reinserted through the opening of the sheath.

The invention also provides a safety device for a syringe, the device comprising a protective sheath in which the syringe can slide, said sheath presenting an opening at a distal portion, which opening is suitable for allowing the syringe to project beyond the sheath, characterized in that the sheath is radially deformable at its distal portion between a rest configuration in which its opening presents a minimum diameter, and a deformed configuration enabling a cylinder to pass through the opening, said cylinder being of a diameter greater than the minimum diameter of the opening.

Figure 1:
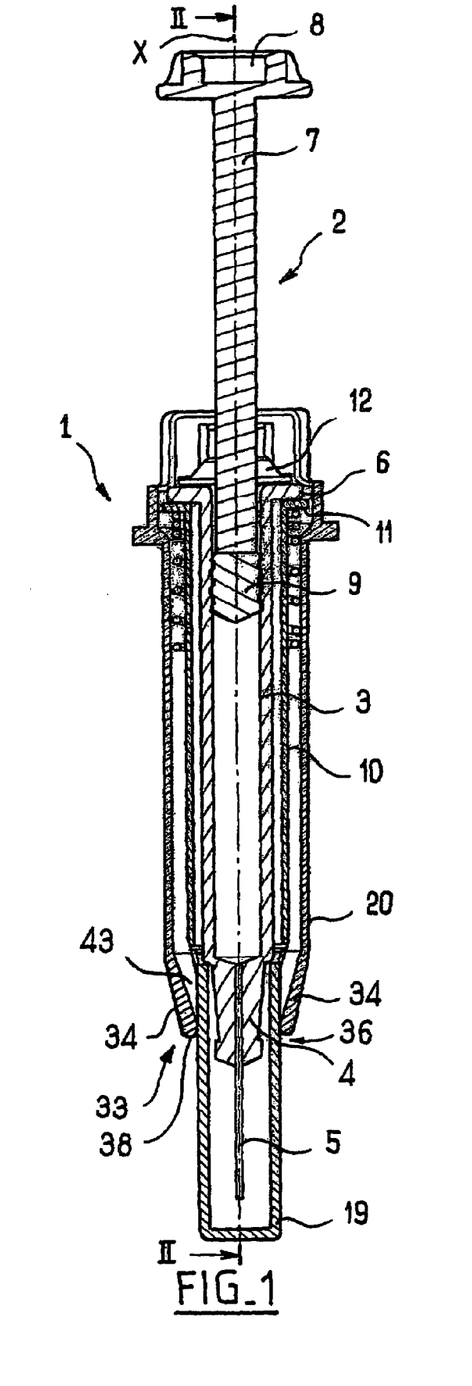
FIG. 1 is a diagrammatic and fragmentary view in axial section of a syringe fitted with a safety device in accordance with a first embodiment of the invention, prior to injection.

The invention will be better understood on reading the following detailed description of non-limiting embodiments, and on examining the accompanying drawings, in which:

FIG. 1 shows a single-use safety device 1 in accordance with the invention fitted to a prefilled syringe 2.

Figure 7:
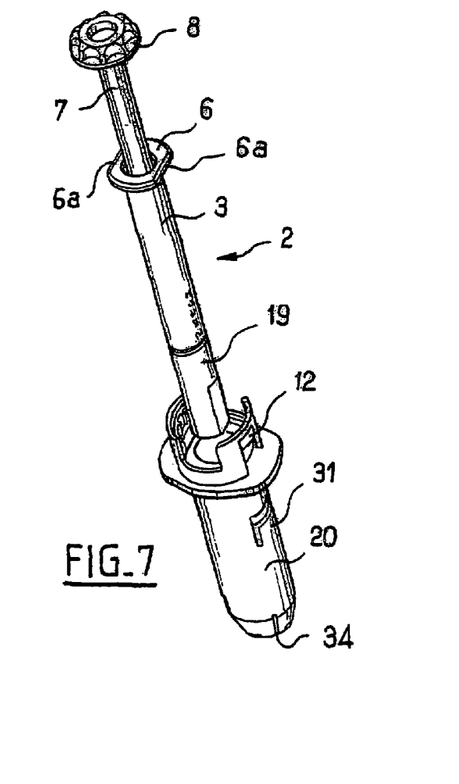
FIG. 7 is a diagrammatic and fragmentary view in perspective of the FIG. 1 syringe and device, prior to being assembled together.

The capacity of the syringe 2 is 0.5 mL. It comprises a cylinder 3 of axis X fitted at its distal end with a needle carrier 4 having a needle 5 mounted thereon. At its proximal end, the syringe cylinder 3 carries a head or collar 6. This portion presents two parallel straight edges 6a, as can be seen in FIG. 7. A piston 9 movable inside the cylinder of the syringe serves to inject the substance contained therein, the piston 9 being actuated by a piston rod 7 terminated by a pushbutton 8 on which the user exerts thrust in order to inject the substance.

In the description below, the terms "top" and "bottom" refer to the orientation selected for FIGS. 1 and 2 in which the needle 5 of the syringe points towards the bottom of the page.

The needle 5 is initially protected by a cap 19 which the user removes prior to making an injection.

The safety device 1 comprises a sleeve 10 in which the cylinder 3 of the syringe is engaged.

Figure 6:
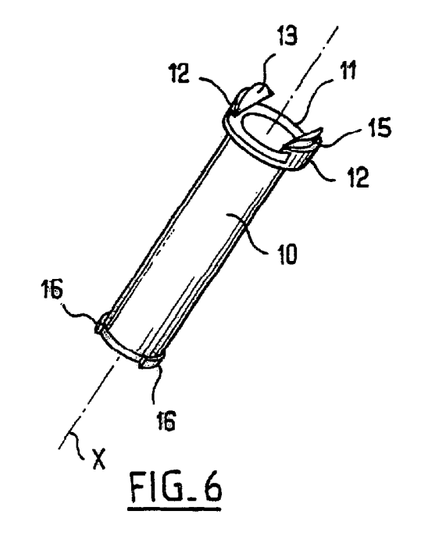
FIG. 6 is a diagrammatic and fragmentary view in perspective of the sleeve of the FIG. 1 device.

The sleeve 10, shown on its own in FIG. 6, is constituted over a major fraction of its length by a cylindrical tube that is circularly symmetrical about the axis X and that has a solid wall. At its proximal end, the sleeve 10 has a collar 11 and two elastically-deformable grip tabs 12 that are diametrically opposite and that are connected to the collar 11 substantially at its periphery.

These tabs 12 enable the syringe head 6 to be held on the collar 11.

At its top end, each tab 12 has a sloping flank 13 making it easy for the syringe head 6 to go past the tabs 12 and snap-fasten therewith.

Behind each of the flanks 13, there is formed a notch 15 whose role is explained below.

At its distal end, and on its outside wall, the sleeve 10 has two diametrically opposite studs 16.

Figure 10:
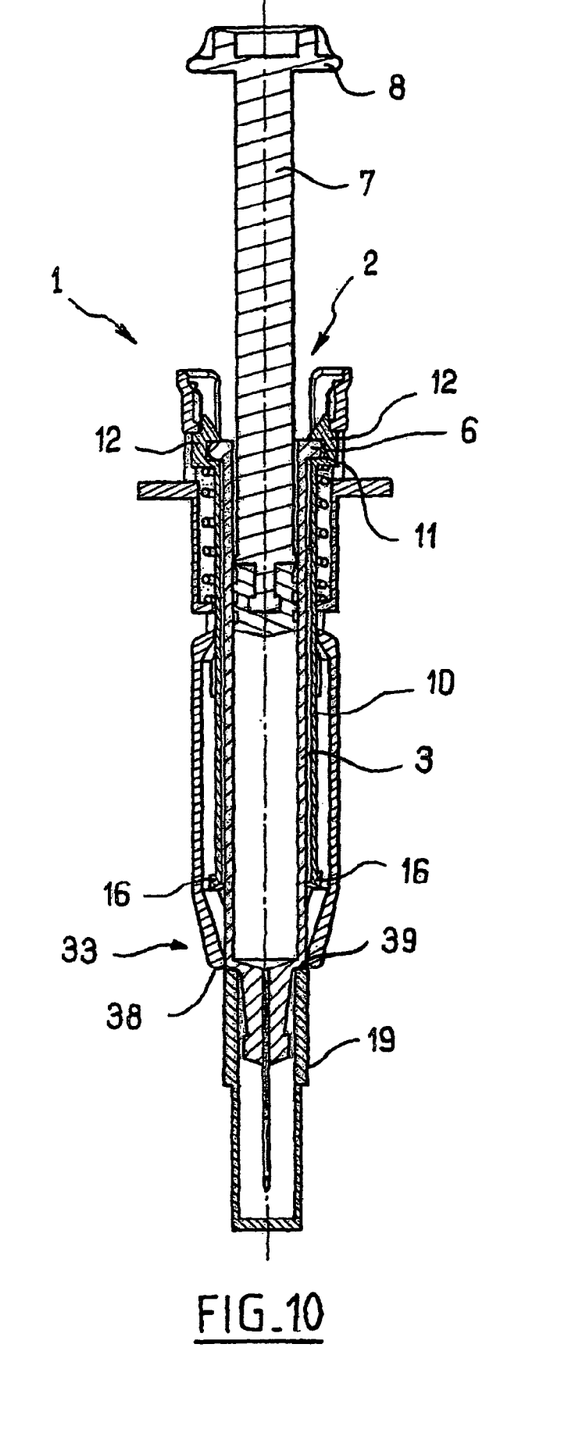
FIG. 10 is a view analogous to that of FIG. 2, the syringe having dimensions that are different from those of the FIG. 2 syringe.

The diameter of the sleeve 10 and the dimensions of the tabs 12 are selected in such a manner as to enable the sleeve to receive two types of syringe, e.g. syringes of the 0.5 mL type and syringes of the 1 mL type, the device 1 fitted with a 1 mL syringe being shown in FIG. 10.

Figures 3, 4, 5:
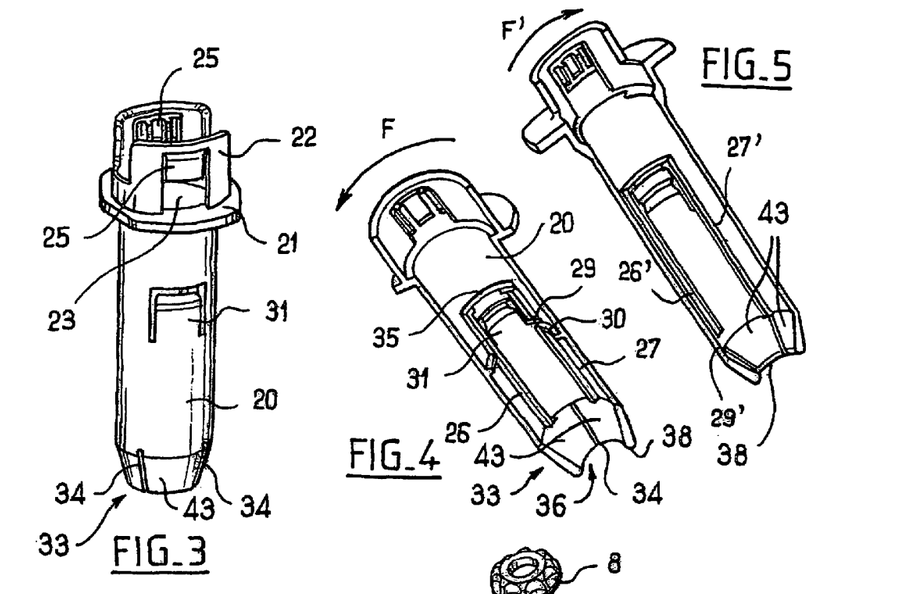
FIG. 3 is a diagrammatic and fragmentary perspective view of the protective sheath of the FIG. 1 device.
FIG. 4 is a diagrammatic and fragmentary view in perspective and in axial section showing the FIG. 3 sheath.
FIG. 5 is a view analogous to that of FIG. 4 showing a sheath in accordance with a variant embodiment of the invention.

The sleeve 10 is for insertion into a protective sheath 20 shown in isolation in FIG. 3. At its proximal end, the protective sheath 20 has a collar 21 having a generally tubular top wall 22 connected thereto. The collar 21 serves as a bearing surface for the fingers of a user proceeding with an injection.

The tubular wall 22 has two windows 23, each presenting a top edge to which a retaining tab 25 is connected. This tab is suitable for being moved away radially by elastic deformation.

The bottom portions of the windows 23 that are not occupied by the retaining tabs 25 leave a passage for the grip tabs 12 of the sleeve 10.

Figure 2:
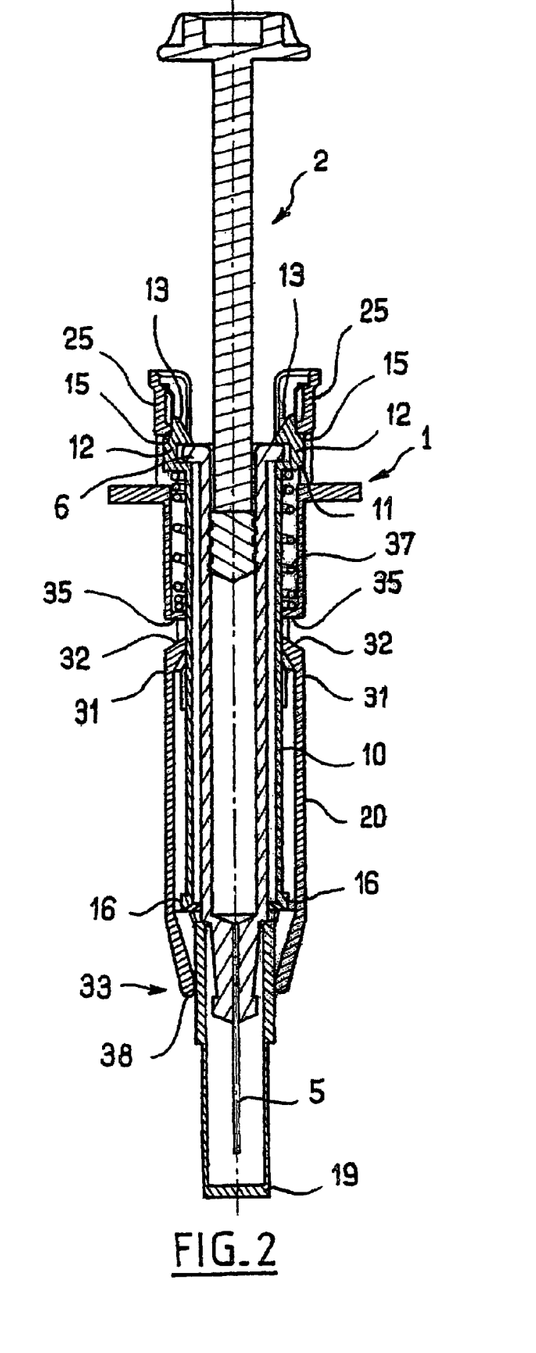
FIG. 2 is a diagrammatic and fragmentary view in axial section on II-II showing the syringe and the device of FIG. 1.

As can be seen in FIG. 2, when the sleeve 10 is in place in the sheath 20, the retaining tabs 25 engage in respective notches 15 of the grip tabs 12, thereby enabling the sleeve 10 to be retained in the sheath 20.

The pushbutton 8 is of a diameter that is sufficient to come into contact with the retaining tabs 25 so as to move them apart at the end of injection.

On its inside wall, the protective sheath 20 has four longitudinally-extending guide splines disposed in pairs, the splines 26 and 27 of a pair leaving between them a gap that enables the studs 16 of the sleeve 10 to engage between them.

The spline 27 is interrupted so as to form a passage 29. In register with the spline 27 there is formed an abutment 30 that is positioned relative to the passage 29 in such a manner that when a stud comes to bear against the abutment 30, it is in register with the passage 29 and can become engaged therein by turning the sleeve 10 relative to the sheath 20.

The sheath 20 also has two elastically-deformable locking tabs 31 made in its wall.

Each locking tab 31, situated between two splines 26 and 27 of a pair, includes an outwardly-directed curved end 32.

The curved ends 32 are situated above the abutments 30 so that when the sleeve 10 is being engaged in the sheath 20, the studs 16 do not need to go past the locking tabs 31.

In its distal portion 33, the protective sheath 20 is generally frustoconical in shape, converging downwards. This portion has four slots 34 giving it a degree of radial resilience, thus enabling it to receive the cap 19, or as explained below, another cylinder of diameter greater than that of the distal opening 36 of the sheath 20.

Figure 9:
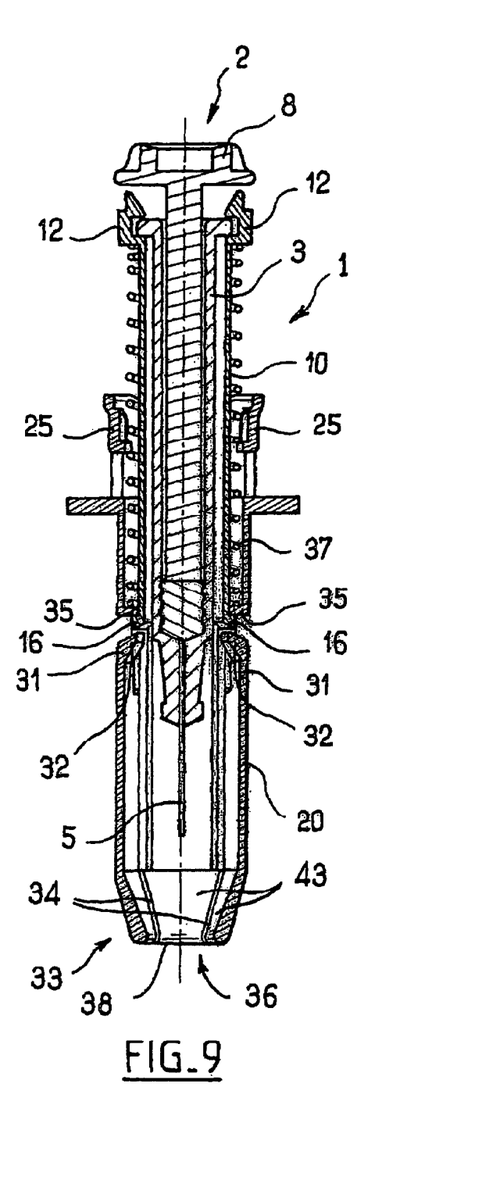
FIG. 9 is a view analogous to that of FIG. 2, after injection, the needle being withdrawn into the protective sheath.

More precisely, the sheath 20 is radially deformable at its distal end between a rest configuration as shown in FIG. 9 where its opening 36 presents a minimum diameter, and a deformed configuration as shown in particular in FIG. 1, that allows a cylinder to pass through the opening 36, said cylinder presenting a diameter that is greater than the minimum diameter of the opening 36.

As described above, the cylinder may be the cap 19 for protecting the needle 5 of the syringe 2, as shown in FIG. 1, from which it can be seen that prior to injection the cap 19 is mounted in such a manner as to project from the sheath 20 through the opening 36.

The sheath 20 thus clamps onto the cap 19, and exerts a force thereon that opposes withdrawal of the cap, and that is sufficient to ensure that the cap 19 does not become separated in untimely manner from the syringe 2.

This reduces the danger of injury and contamination due to accidental contact of the needle 5 with a person other than the patient who is to be injected.

In addition, as can be seen in FIG. 10, the sheath 20 and the cap 19 are arranged in such a manner as to prevent the cap 19 from being reinserted into the sheath 20 through its opening 26 after the cap 19 has been withdrawn.

Once the cap 19 has been withdrawn, the distal portion of the sheath 20 contracts so that the opening 36 presents a diameter smaller than the outside diameter of the cap 19. Specifically, the distal portion of the sheath clamps onto the syringe cylinder 3.

More precisely, although the opening 36 presents a rounded edge 38, beside its opening, the cap 19 presents a straight edge 39 which comes into abutment against the rounded edge 38 of the opening 36.

Figure 11:
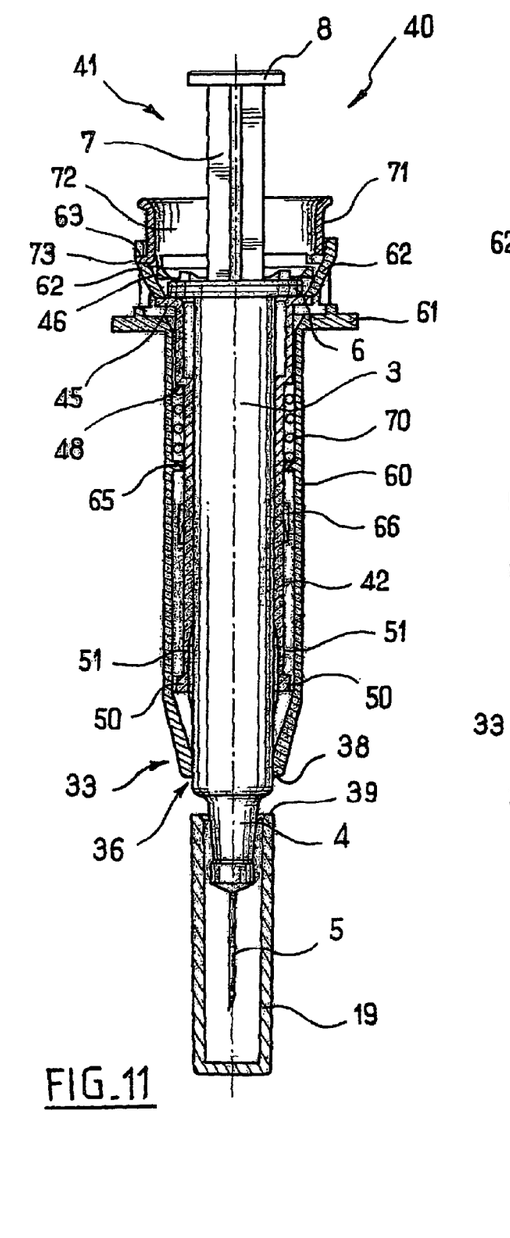
FIG. 11 is a diagrammatic and fragmentary view in axial section of a syringe fitted with a safety device in accordance with another embodiment of the invention, shown prior to injection.

Another cylinder suitable for being received in the sheath 20 through the opening may be constituted by the syringe cylinder 3 as shown in FIGS. 10 and 11 where, as explained below, there can be seen a syringe 2 of size that is greater (in terms of diameter and length) than the syringe 2 shown in FIGS. 1 and 2.

Figure 12:
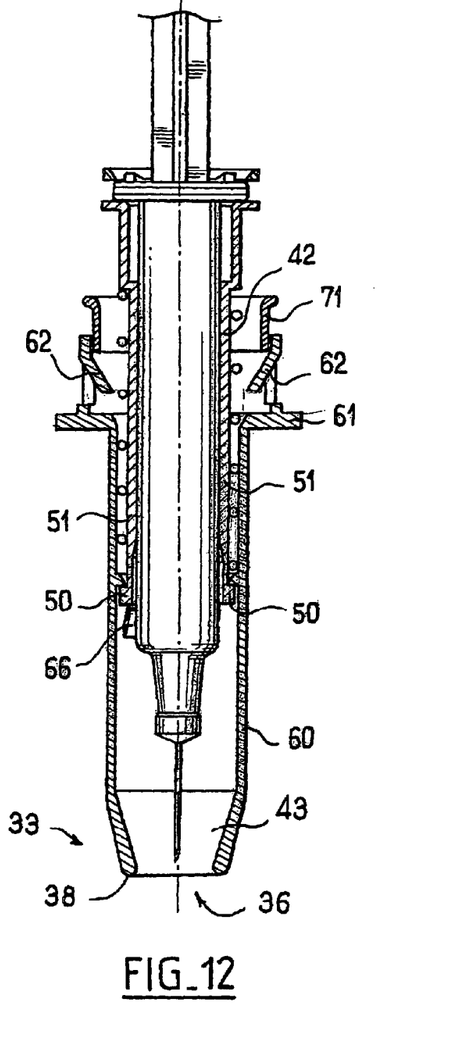
FIG. 12 is a view analogous to that of FIG. 11, after injection, the needle being withdrawn into the protective sheath.

As can be seen in FIGS. 11 and 12, the syringe cylinder 3 is of a length such that while it is in its configuration prior to injection and during injection, it projects beyond the sheath 20 through the opening 36.

Because of the radial resilience of its distal portion 33, the sheath 20 clamps onto the syringe cylinder 3, which in this case presents a diameter greater than the minimum diameter of the opening 36. This ensures that the syringe cylinder 3 is held gripped close to the needle carrier 4.

This grip, combined with the grip on the syringe head 6 provided by the sleeve 10, ensures that the syringe 2 is held rigidly within the sheath 20, thus benefiting the safety and the accuracy of injection operations.

The sheath 20 may be made by molding. The mold used (not shown) comprises by way of example a stationary outer portion having a hollow within which there slides a substantially cylindrical moving portion, the mold cavity being formed between the stationary and moving portions.

Thus, another cylinder suitable for being received in the sheath 20 through the opening 36 may be constituted by the moving portion of the mold, which during unmolding, is withdrawn from the sheath 20 in the axial direction through the opening 36. This withdrawal is made easier by the radial resilience of the distal portion 33 of the sheath 20.

As explained above, in order to make such radial resilience possible, the distal portion 33 of the sheath 20 is pierced by a plurality of slots 34, in this case four slots, although some other number of slots (e.g. two or six) could also be envisaged.

These slots 34, which extend longitudinally and open out into the opening 36, define elastically flexible tongues 43 which converge downwards and give the sheath 20 its radial resilience.

The sheath 20 also has two internal transverse shoulders 35 extending between the guide splines 26 and 27 of a pair and situated above the curved end 32 of the locking tabs 31.

The device 1 includes a helical spring 37 installed around the sleeve 10 and bearing at one end against the shoulders 35 and at its other end against the collar 11.

The sleeve 10 is mounted in the sheath 20 as follows.

Initially, the sleeve 10 is positioned relative to the sheath 20 in such a manner that the two grip tabs 12 are positioned between the two retaining tabs 25 of the sheath 20.

The sleeve 10 is inserted into the sheath 20 while maintaining this relative position, with this initial insertion movement being continued until the studs 16 of the sleeve 10 come to bear against the abutments 30 of the sheath 20.

As shown in FIG. 4, the sleeve 10 is then turned in the direction of arrow F through one-fourth of a turn relative to the sheath 20, so as to cause each of the studs 16 to pass through a respective passage 29.

After turning in this way, the stud 16 is received between the splines 26 and 27, and the sleeve 10 has a second insertion movement applied thereto, urging it into the sheath 20. The studs 16 engaged between the splines 26 and 27 then guide the sleeve 10 relative to the sheath 20. This movement is continued until the grip tabs 12 snap under the retaining tabs 25.

Once the sleeve 10 and the sheath 20 have been assembled together, the prefilled syringe 2 is inserted into the sleeve 10, with the syringe head 6 being positioned in such a manner that the straight sides 6a thereof face the grip tabs 12, as can be seen in FIG. 7.

The head 6 snap-fastens on the grip tabs 12 in such a manner as to be retained against the collar 11.

The studs 16 engaged between the splines 26 and 27 prevent the sleeve 10 from turning relative to the sheath 20.

In the example described above, one of the splines is interrupted. In a variant, as shown in FIG. 5, all of the splines may be continuous, and one of the splines 26' may terminate before the other spline 27', so that the spline 26' is shorter than the other.

A bottom passage 29' is thus provided beneath the spline 26', enabling a stud 16 of the sleeve 10 to be inserted between the two splines 26' and 27' by turning the sleeve 10 through one-fourth of a turn in the direction of arrow F' relative to the sheath 20.

In this embodiment, only one axial insertion movement is required followed by a turning movement.

The operation of the safety device 1 is as follows.

To inject the substance contained in the syringe 2, the user applies thrust to the pushbutton 8 so as to push in the piston 9.

Figure 8:
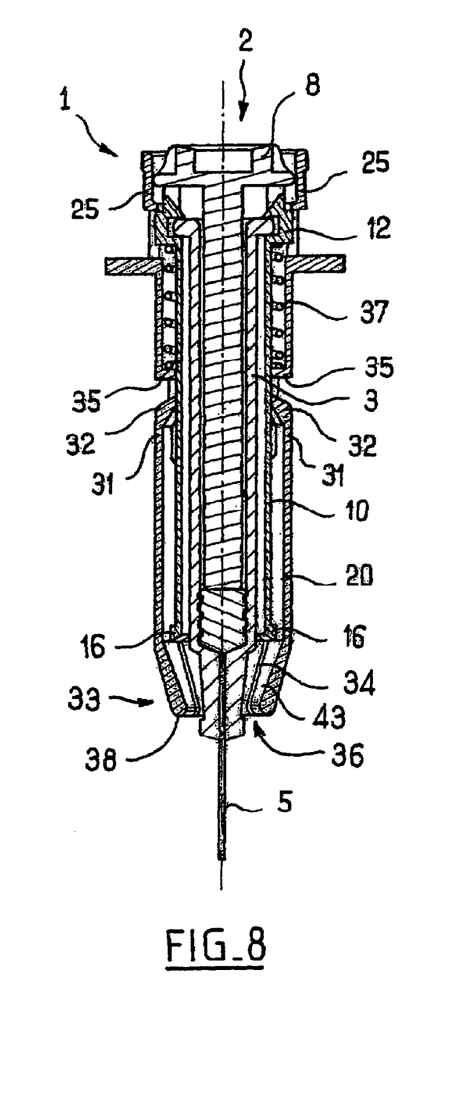
FIG. 8 is a view analogous to that of FIG. 2, at the end of injection.

At the end of the stroke of the piston 9 into the syringe cylinder 3, the pushbutton 8 causes the retaining tabs 25 to be moved apart so as to release the sleeve 10, whereupon the spring 37 causes the assembly constituted by the sleeve 10 and the syringe 2 to move rearwards, as can be seen in FIG. 8.

During this rearward movement, the studs 16 on the sleeve 10 go past the locking tabs 31 of the sheath 20.

At the end of the stroke, as shown in FIG. 9, the studs 16 come into abutment against the shoulders 35, and the needle 5 has been withdrawn into the sheath 20.

The studs 16 which are engaged above the curved ends 32 of the tabs 31 prevent the sleeve 10 from moving towards the distal end of the sheath 20.

This serves to lock the device 1 in its safe position, after injection has taken place.

FIGS. 11 to 14 show a safety device 40 constituting another embodiment of the invention.

This safety device 40 is arranged in such a manner as to receive a standard syringe 41 having 0.5 mL or 1 mL capacity, substantially analogous to the above-described syringe 2.

The safety device 40 has a sleeve 42 in which the syringe cylinder 3 is engaged. As can be seen in particular in FIGS. 13 and 14, the proximal end of the sleeve 42 has means for gripping the collar or head 6 on the syringe cylinder. These grip means comprise a collar 45 connected by a plurality of bridges of material 47, e.g. four bridges of material 47, to a top ring 46, the syringe head 6 being retained between the collar 45 and said ring 46.

Figure 13:
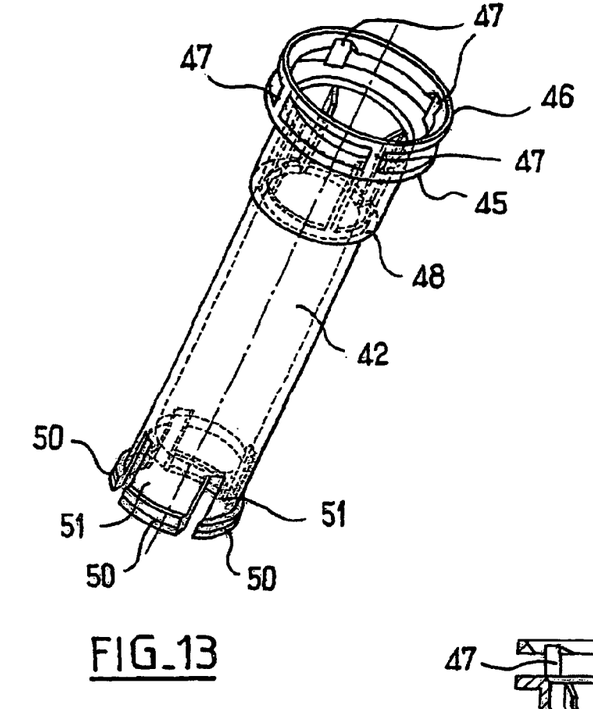
FIG. 13 is a diagrammatic and fragmentary view in perspective of the sleeve of the FIG. 11 safety device.
Figure 14:
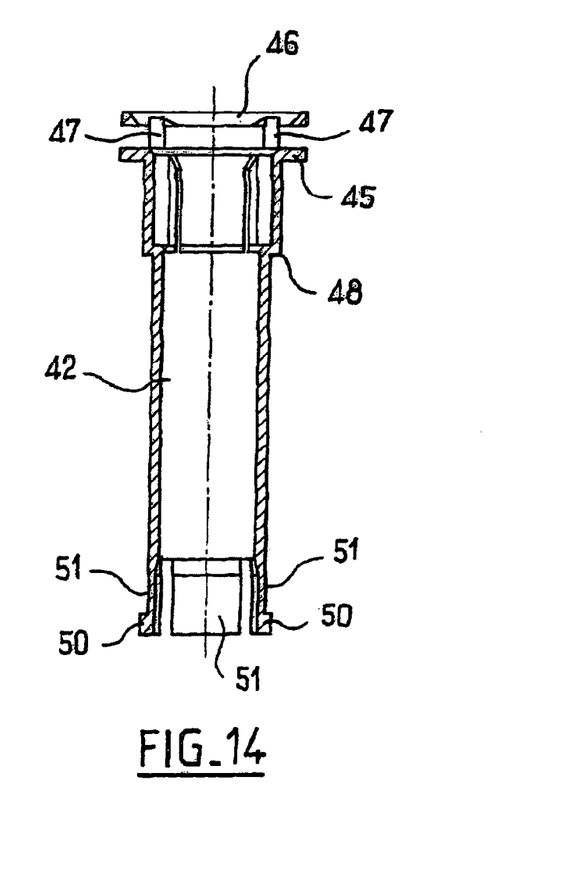
FIG. 14 is a diagrammatic and fragmentary view in axial section of the FIG. 13 sleeve.

The ring 46 defines a top opening presenting in axial section a shape that is generally frustoconical, diverging upwards, serving to guide the syringe head 6 through said opening while the syringe is being mounted in the sleeve 42.

The sleeve 42 also has a shoulder 48 defining an enlargement in the section of its proximal portion.

The sleeve 42 has a plurality of narrow, elastically-deformable tabs 51 at its distal end, with the end of each tab carrying a stud 50.

After assembly, the syringe 2 and the sleeve 42 are prevented from moving relative to each other.

The sleeve 42 is for engaging in a protective sheath 60 having a collar 61 in its proximal portion with a bottom surface that serves as a bearing surface for the fingers of a user during injection.

At its proximal end, the sheath 60 includes a plurality of elastically-deformable retaining tabs 62 beneath the collar 61 which, at rest, are folded inwards.

Between the tabs 62 there are provided openings 63 having a role that is explained below.

In the folded state, the retaining tabs 42 come to bear against the collar 45 of the sleeve 42, thus limiting upward axial displacement of the assembly constituted by the sleeve 42 and the syringe 2.

Substantially halfway along its length in the example described, the protective sheath 60 also includes a discontinuous internal bearing surface 65. The end edge of the bearing surface 65 is generally frustoconical, diverging upwards, thus making it possible, during insertion of the sleeve 10 into the sheath 60, to guide the studs 50 through said bearing surface 65.

The device 40 includes anti-return or locking means defined by locking tabs 66 that are substantially analogous to the locking tabs 31 described above, and that are made in the wall of the sheath 60.

The studs 50 can go past these locking tabs 66.

A helical spring 70 is placed in the sheath 60 around the sleeve 42 bearing respectively against the bearing surface 65 and the shoulder 48.

The safety device 40 also has a button 71 including a cylindrical wall 72 with hooks 73 at its distal end suitable for engaging in the above-mentioned openings 63 in the sheath 60, situated between the tabs 62.

At its proximal end, the cylindrical wall 72 presents an upwardly diverging rim against which the user can apply a thumb in order to depress the pushbutton 71.

The distal edge of the button 71 is for coming into contact with the tabs 62 causing them to move apart.

The safety device 40 operates as follows.

The user inserts the needle 5 under the skin of the patient, with the syringe being prevented from moving in translation relative to the sheath 60. In order to inject the content of the syringe, the user applies the index and middle fingers against the collar 61 so as to enable the thumb to press against the head 8 with sufficient force to inject the substance.

At the end of the stroke of the piston rod 7 inside the cylinder 3, the user makes use of the thumb which is pressed against the head 8 of the piston to depress the button 71 without performing any additional action other than that which gave rise to injection, thereby moving apart the tabs 62 and releasing the sleeve 42. The assembly constituted by the syringe 2 and the sleeve 42 can then be driven upwards under drive from the spring 70.

During this upward displacement, the studs 50 go past the locking tabs 66 and come into abutment against the bearing surface 65, thus limiting the upward stroke of the assembly constituted by the syringe 2 and the sleeve 42, as can be seen in FIG. 12.

The needle 5 is then withdrawn inside the protective sheath 60 so it no longer presents any danger of contamination and/or injury after injection.

Furthermore, the studs 50 engage above the tabs 66 prevent the sheath from being pushed out from the protective sheath 60, thus serving to lock the safety device 1, after use.

In the example described, the button 70 is constituted by a separate element which is fixed on the protective sheath 60.

Figure 15:
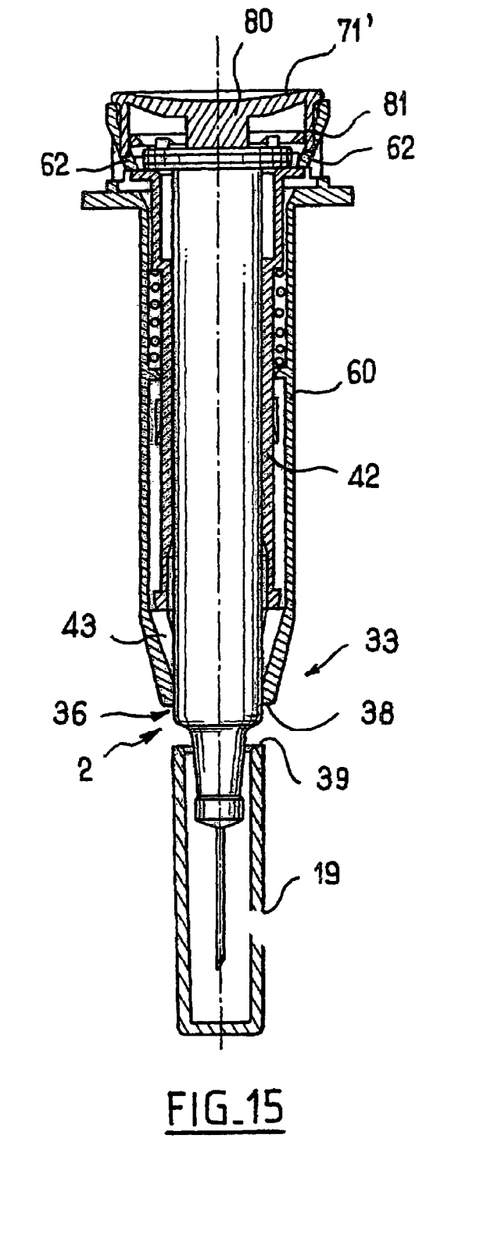
FIG. 15 is a diagrammatic and fragmentary view in axial section of a syringe fitted with a safety device in accordance with another embodiment of the invention.

In a variant, and as shown in FIG. 15, the safety device includes a button 71' that is made integrally with the head 8 of the piston rod 7. This pushbutton 71' has a concave surface 80 in its top portion enabling the user to press a thumb thereagainst.

The button 71' has a skirt 81 extending beneath the surface 80 and serving, when the piston rod 7 is substantially at the end of its injection stroke, to move apart the retaining tabs 62 and thus release the assembly constituted by the syringe 2 and the sleeve 42.

Figure 16:
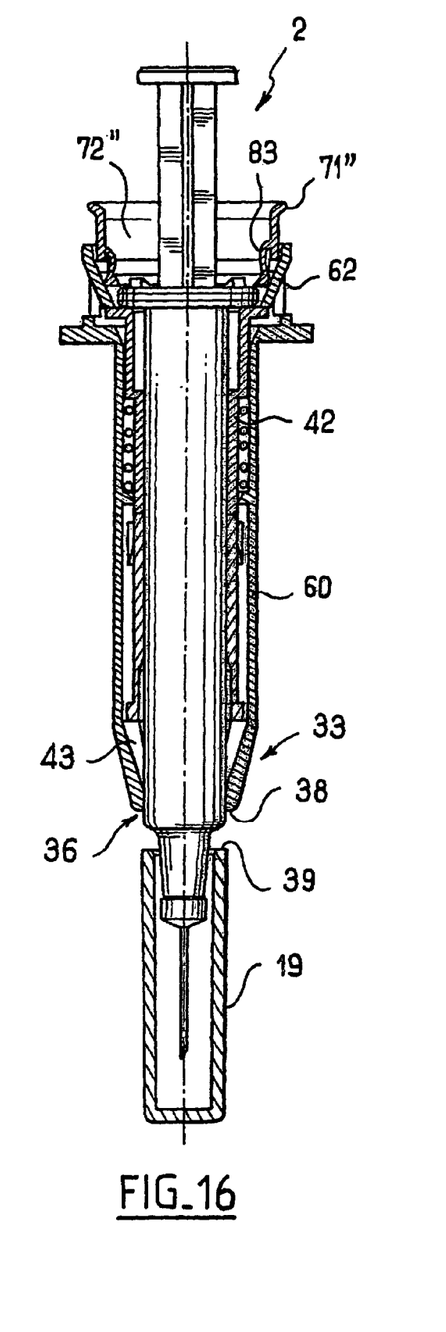
FIG. 16 is a diagrammatic and fragmentary view in axial section of a syringe fitted with a safety device in accordance with another embodiment of the invention.

In another variant, as shown in FIG. 16, the safety device has a button 71". This button comprises a cylindrical wall 72" which is connected to the sleeve 42 via elastically-deformable arms 83.

In the example described, the cylindrical wall 72", the elastically-deformable arms 83, and the sleeve 42 are made as a single piece.

At the end of injection, the pushbutton 71" is pushed in and the wall 72" causes the tabs 62 to move apart so as to release the sleeve 42.

Figure 17:
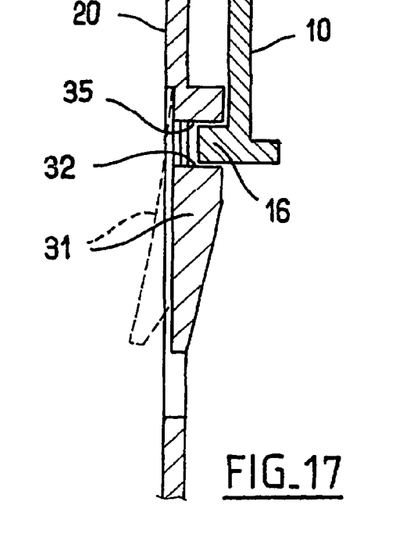
FIG. 17 is a diagrammatic and fragmentary axial section view of the sleeve of a device of the kind shown in the preceding figures, in accordance with another embodiment.
Figure 18:
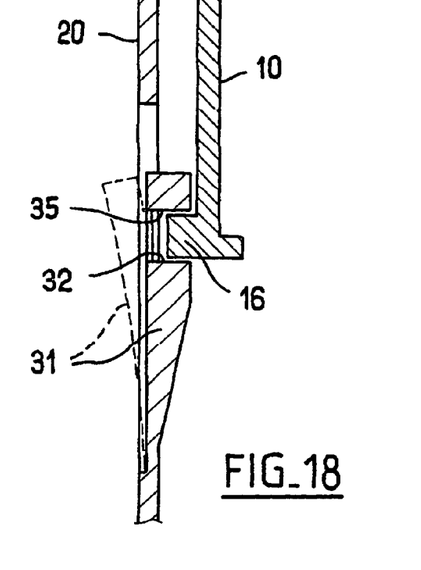
FIG. 18 is a view analogous to FIG. 17, in a variant embodiment.
Figure 19:
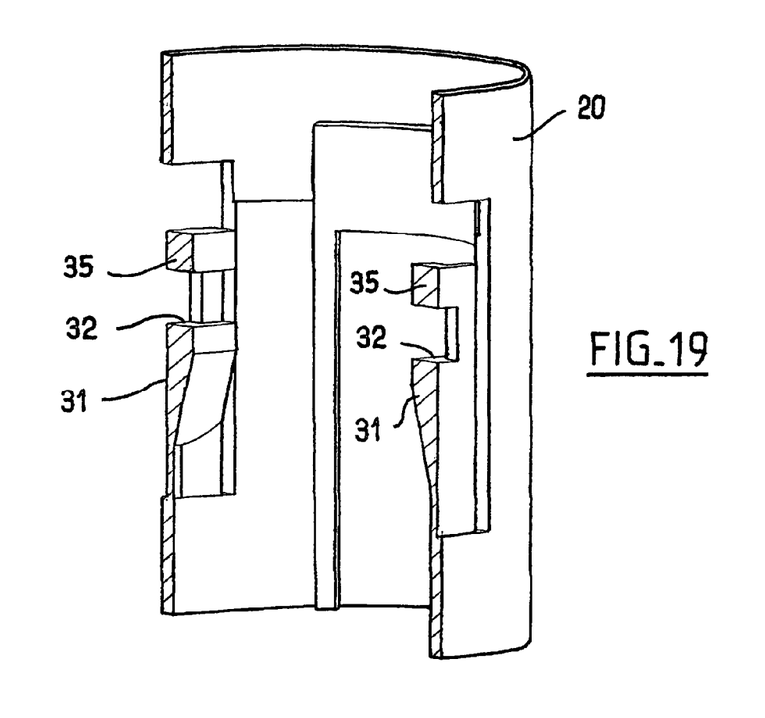
FIG. 19 is a diagrammatic and fragmentary view in perspective and in axial section of the FIG. 18 sleeve.

FIGS. 17 to 19 show two variant embodiments in which the shoulder 35 and the curved end 32 both belong to the same resiliently deformable tab 32 suitable for being pushed outwards, as represented in FIGS. 17 and 18 by dashed lines, under the effect of a radial force exerted outwards from the center of the sheath 20.

This feature makes it easier to insert the sleeve 10 during assembly of the device 1. By moving the tabs 31 outwards, the shoulders 35 are moved away from the path of the studs 16, which have no difficulty in going past the tabs 31 so as to become positioned in the distal portion 35 of the sheath 20 (configuration shown in particular in FIG. 8).

As a result, there is no need to ensure that the sleeve 10 is in any particular orientation on being inserted into the sheath 20.

Conversely, after injection, the sleeve 10 reverses in the sheath, the studs 16 going past the locking tabs 31 by moving them outwards until they become positioned, in the space left between the portions 32 and the shoulders 35, as shown in FIGS. 17 and 18, the sleeve 10 then being prevented from moving in the position it has thus reached, thereby locking the device 1 in its safe position.

This structural feature also simplifies fabrication of the sheath 20 since there is no need to provide an outer mold in two parts with a join plane extending between the shoulders 35 and the portions 32 of the tabs 31.

Given the radial resilience of the tabs 31 including both the portions 32 and the shoulders 35, the sheath 20 can be molded by means of two mold parts, a stationary outer part constituted by a single piece and an inner part that is movable in translation inside the outer part and that can be withdrawn towards the proximal end of the sheath 20 while moving apart the tabs 31 as it goes through.

As can be seen in FIGS. 17 to 19, the tabs 31 may be attached to a top portion of the sheath 20, situated beside its proximal portion (FIG. 17), or to a bottom portion of the sheath 20, situated beside its distal portion 33 (FIGS. 18 and 19).

The invention claimed is:

1. A safety device for a syringe, the device comprising:
   (a) a protective sheath presenting at a distal portion, an opening, which is suitable for allowing the syringe to project beyond the sheath, and the protective sheath presenting at the distal portion a radial resilience suitable for enabling the sheath to receive a cylinder of a diameter greater than that of said opening,
   (b) means for enabling the syringe to slide in the sheath between a first position enabling injection to be performed and a second position in which the needle of the syringe is withdrawn into the inside of the sheath,
   (c) a sleeve radially inward from said protective sheath along a portion of the sheath, the sleeve being suitable for receiving the syringe, and
   (d) a resilient element acting between the sheath and the sleeve, the resilient element enabling the sleeve to move, at the end of injection, from the first position into the second position by a rearward movement of the sleeve relative to the sheath.

2. A device according to claim 1, wherein said cylinder is a cap for protecting the needle of the syringe.

3. A device according to claim 1, wherein said cylinder is the cylinder of the syringe.

4. A device according to claim 1, wherein the sheath is made by molding, and said cylinder is a moving portion of a mold.

5. A device according to claim 1, wherein the shape of the distal portion of the sheath is frustoconical.

6. A device according to claim 1, wherein the distal portion of the sheath is split.

7. A device according to claim 6, wherein the distal portion of the sheath has a plurality of longitudinal slots defining converging resilient tongues.

8. A device according to claim 1, wherein a grip means is arranged to grip a collar forming the head of the syringe.

9. A device according to claim 1, wherein the safety device is fitted to said syringe.

10. A device according to claim 9, further comprising a cap protecting the needle of the syringe.

11. A device according to claim 10, wherein said cap is mounted in such a manner as to project beyond the sheath through the distal opening thereof.

12. A device according to claim 11, wherein the sheath and the cap are arranged in such a manner as to act, after the cap has been removed, to prevent the cap from being reinserted through the opening of the sheath.

13. A safety device for a preexisting syringe, the device comprising:
   (a) a protective sheath presenting at a distal portion, an opening, which is suitable for allowing the syringe to project beyond the sheath, and the protective sheath presenting at the distal portion a radial resilience suitable for enabling the sheath to receive a cylinder of a diameter greater than that of said opening,
   (b) means for enabling the syringe to slide in the sheath between a first position enabling injection to be performed and a second position in which the needle of the syringe is withdrawn into the inside of the sheath,
   (c) a sleeve suitable for receiving the syringe, and
   (d) a resilient element acting between the sheath and the sleeve, the resilient element enabling the sleeve to move, at the end of injection, from the first position into the second position by a rearward movement of the sleeve relative to the sheath, wherein the device is configured to receive at least two different sizes of preexisting syringes.

14. A safety device for a syringe, the device comprising:
   (a) a protective sheath comprising a cylindrical body having a portion of constant diameter and a distal portion extending from the body, the distal portion defining an opening suitable for allowing the syringe to project beyond the sheath, and the distal portion having a radial resilience suitable for enabling the sheath to receive a cylinder of a diameter greater than that of said opening,
   (b) means for enabling the syringe to slide in the sheath between a first position enabling injection to be performed and a second position in which at least a major portion of the needle of the syringe is withdrawn into the inside of the portion having constant diameter of the cylindrical body of the sheath,
   (c) a sleeve suitable for receiving the syringe, and
   (d) a resilient element acting between the sheath and the sleeve, the resilient element enabling the sleeve to move, at the end of injection, from the first position into the second position by a rearward movement of the sleeve relative to the sheath.

15. A device according to claim 14, wherein said cylinder is a cap for protecting the needle of the syringe.

16. A device according to claim 14, wherein said cylinder is the cylinder of the syringe.

17. A device according to claim 14, wherein the shape of the distal portion of the sheath is frustoconical.

18. A device according to claim 14, wherein the distal portion of the sheath is split.

19. A device according to claim 18, wherein the distal portion of the sheath has a plurality of longitudinal slots defining converging resilient tongues.

20. A device according to claim 14, wherein a grip means is arranged to grip a collar forming the head of the syringe.

21. A device according to claim 1, wherein the resilient element is in direct physical contact with the sheath and the sleeve.

22. A device according to claim 1, wherein the sheath is configured to receive said cylinder on an inner surface of the distal portion of the sheath.

* * * * *

UNITED STATES PATENT AND TRADEMARK OFFICE
CERTIFICATE OF CORRECTION

PATENT NO.        : 8,337,467 B2
APPLICATION NO.   : 10/492625
DATED             : December 25, 2012
INVENTOR(S)       : Rimlinger et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1475 days.

Signed and Sealed this
Twenty-fourth Day of June, 2014

Michelle K. Lee
*Deputy Director of the United States Patent and Trademark Office*